US007006859B1

(12) United States Patent
Osorio et al.

(10) Patent No.: US 7,006,859 B1
(45) Date of Patent: Feb. 28, 2006

(54) UNITIZED ELECTRODE WITH THREE-DIMENSIONAL MULTI-SITE, MULTI-MODAL CAPABILITIES FOR DETECTION AND CONTROL OF BRAIN STATE CHANGES

(75) Inventors: Ivan Osorio, Leawood, KS (US); Naresh C. Bhavaraju, Lawrence, KS (US)

(73) Assignee: Flint Hills Scientific, L.L.C., Lawrence, KS (US)

( * ) Notice: Subject to any disclaimer, the term of this patent is extended or adjusted under 35 U.S.C. 154(b) by 158 days.

(21) Appl. No.: 10/622,238

(22) Filed: Jul. 18, 2003

Related U.S. Application Data

(60) Provisional application No. 60/397,511, filed on Jul. 20, 2002.

(51) Int. Cl.
*A61B 5/042* (2006.01)
*A61N 1/05* (2006.01)
(52) U.S. Cl. ...................................... 600/378; 607/116
(58) Field of Classification Search ................ 600/378; 607/116
See application file for complete search history.

(56) References Cited

U.S. PATENT DOCUMENTS

| | | | | |
|---|---|---|---|---|
| 3,826,244 A | * | 7/1974 | Salcman et al. ............. | 600/378 |
| 4,245,645 A | * | 1/1981 | Arseneault et al. ......... | 600/378 |
| 4,735,208 A | | 4/1988 | Wyler et al. | |
| 4,903,702 A | | 2/1990 | Putz | |
| 5,097,835 A | | 3/1992 | Putz | |
| 5,215,088 A | * | 6/1993 | Normann et al. ........... | 600/378 |
| 5,938,689 A | | 8/1999 | Fischell et al. | |
| 5,995,868 A | | 11/1999 | Dorfmeister et al. | |
| 6,171,239 B1 | * | 1/2001 | Humphrey .................. | 600/378 |
| 6,560,472 B1 | * | 5/2003 | Hill et al. ................... | 600/378 |

OTHER PUBLICATIONS

Topographic and Toposcopic Study of Origin and Spread of the Regular Synchronized Arousal Pattern in the Rabbit, by H. Petsche and Ch. Stumpf, *EEG and Clin. Neurophysiol.* 12:589-600 (1960).
The Significance of the Cortex for the Travelling Phenomena of Brain Waves, by H. Petsche and J. Štere, *Electroenceph. Clin Neurophysiol*, 25:11-22 (1968).
Étude sur Modèle des Méthodes de Détection EEG, by L. Jami, A. Fourment. J. Calvet et M. Thiefry, *Electroenceph. Clin. Neurophysiol.* 24:130-145 (1968).

(Continued)

*Primary Examiner*—Lee S. Cohen
(74) *Attorney, Agent, or Firm*—Donald R. Schoonover

(57) ABSTRACT

An electrode with three-dimensional capabilities for detection and control of brain state changes of a subject. The electrode includes a disk portion having an upper surface and a lower surface, and a shaft portion secured to and extending perpendicularly outwardly from the lower surface of the disk portion; the shaft portion having an outer surface. The disk portion and shaft portion may include one or more recording or stimulating contact surfaces structured to operatively interact with the brain of a subject. Insulating material isolates each of the recording or stimulating contact surfaces from each other. At least one conductor operatively and separately connect each of the recording or stimulating contact surfaces in communication with external apparatus. The disk portion and shaft portion are structured relative to each other to operatively provide support and anchoring for each other while providing three-dimensional capabilities for detection and control of brain state changes of a subject. Modified embodiments include insertible/retractable electrode wires, both contained in channels and sheathed in axially displaceable cannulae; activating mechanisms for inserting/retracting the electrode wires and/or cannulae; and multiple shaft portions.

7 Claims, 6 Drawing Sheets

OTHER PUBLICATIONS

Influence of Cortial Incisions on Synchronization Pattern and Travelling Waves, by H. Petsche and P. Rappelsberger, *Electroenceph. Clin. Neurophysiol.* 28:592-600 (1970).

Properties of Cortical Seizure Potential Fields, by H. Petsche, P. Rappelsberger and R. Trappl, *Electroenceph. Clin. Neurophysiol.* 29:567-578 (1970).

Cerebral Cortex: Cytoarchitecture and Electrophysiology, by Elliott M. Marcus, In: "An Introduction to the Neurosciences," by B. A. Curtis, S, Jacobson and E. M. Marcus, Ch. 20, pp. 447-482, W. B. Saunders, Philadelphia (1972).

Real Time Automated Detection and Quantitative Analysis of Seizures and Short Term Predictions of Clinical Onset, by Ivan Osorio, Mark G. Frei and S. B. Wilkinson, *Epilepsia* 39 (16):615-627 (1998).

Seizure Blockage with Automated "Closed-Loop" Electrical Stimulation: A Pilot Study, by Ivan Osorio, Mark G. Frei, S.B. Wilkinson, S. Sunderam, Naresh C. Bhavaraju, N. Graves, S. F. Schaffner, T. Peters, A. M. Johnson, C. A. DiTeresi, J. Ingram, V. Nagaraddi, J. Overman, M. A. Kavalir and M. Tumbull, *Epilepsia* 42(7):(Abstract 2.336) (2001).

An Introduction to Contingent (Closed-Loop) Brain Electrical Stimulation for Seizure Blockage, to Ultra-Short Term Clinical Trials and to Multidimensional Statistical Analysis of Therapeutic Efficacy, by Ivan Osorio, Mark G. Frei, B. F. J. Manly, S. Sunderam, Naresh C. Bhavaraju and S. B. Wilkinson, *J. Clin. Neurophysiol.* 18(6):533-544 (2001).

\* cited by examiner

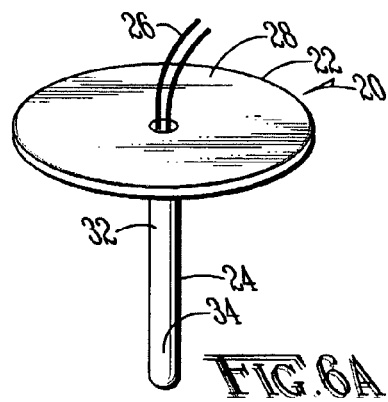
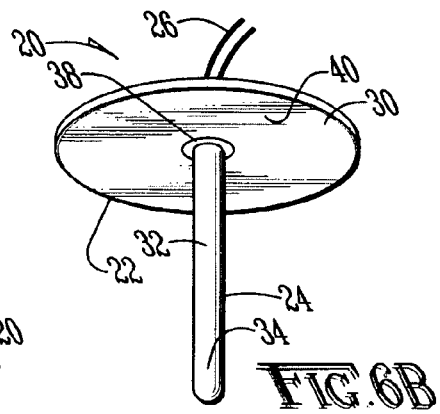
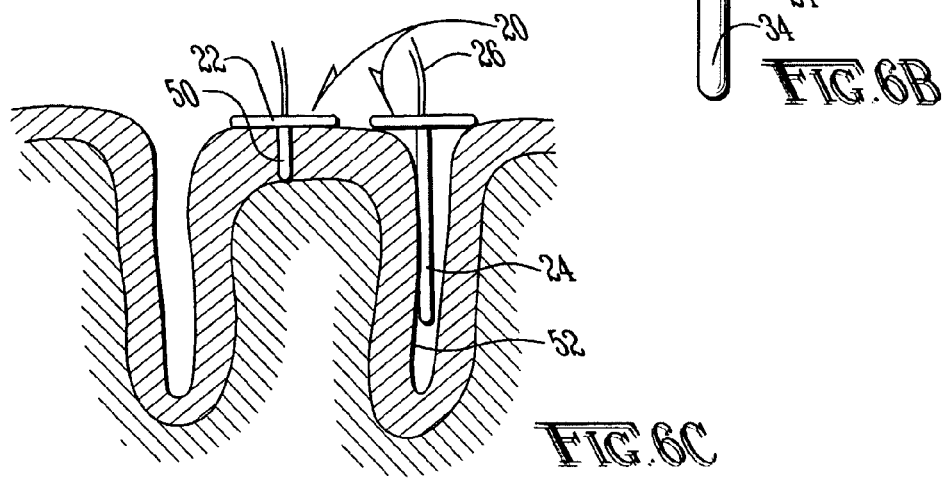
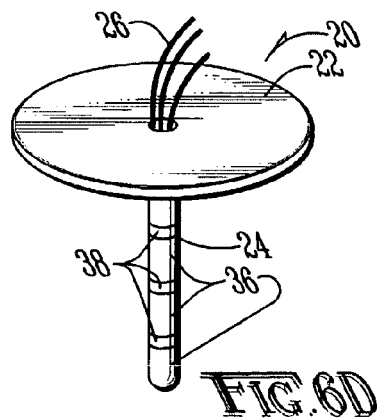
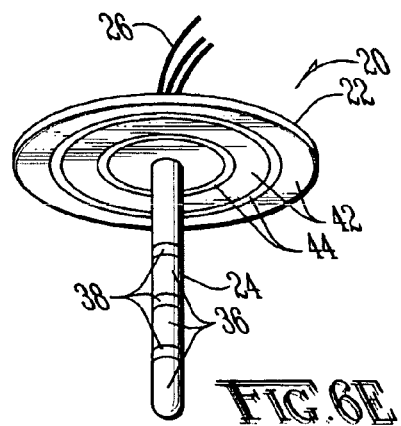

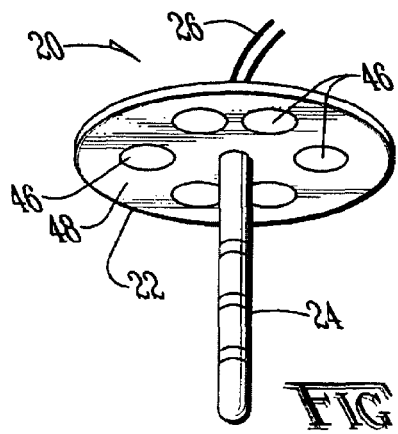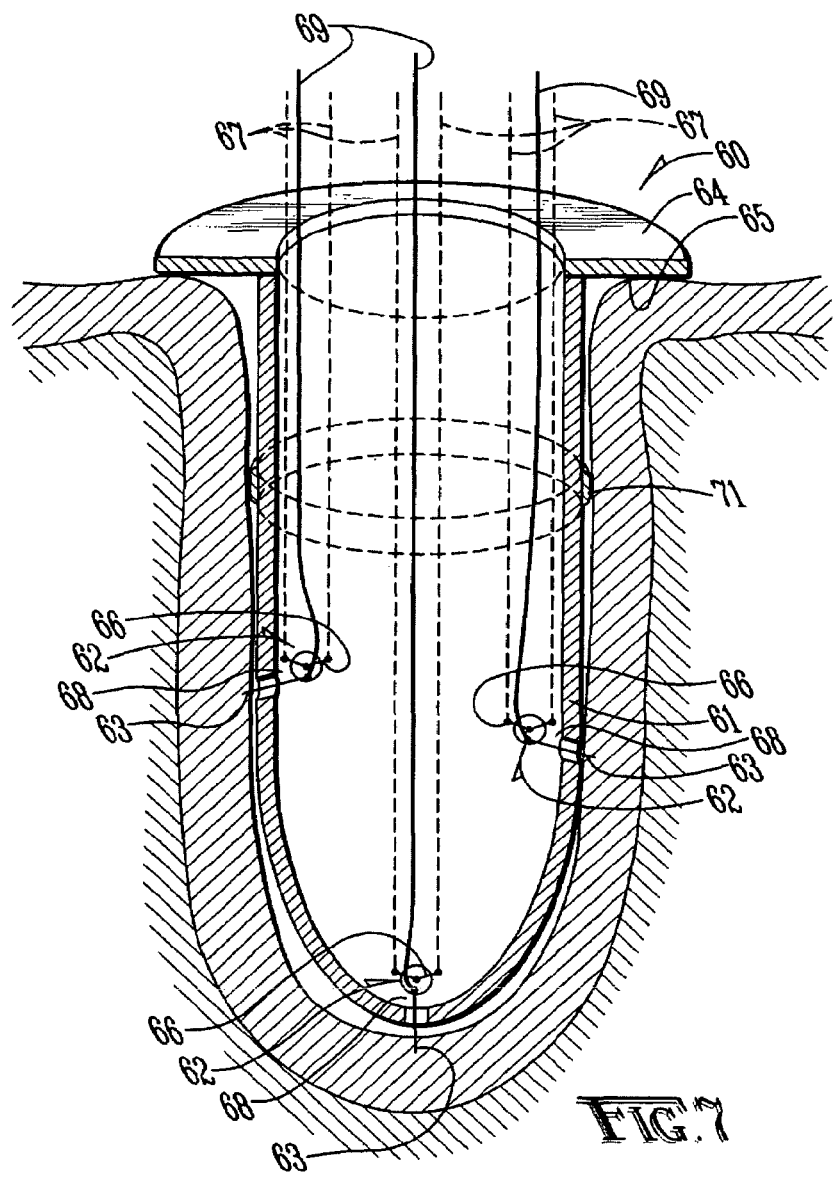

UNITIZED ELECTRODE WITH THREE-DIMENSIONAL MULTI-SITE, MULTI-MODAL CAPABILITIES FOR DETECTION AND CONTROL OF BRAIN STATE CHANGES

CROSS REFERENCE TO RELATED APPLICATIONS

This application is a continuation-in-part of Provisional Patent Application No. 60/397,511 filed Jul. 20, 2002 and entitled "Self-anchoring, Unitized, Mesoelectrode with Multisite, Multimodal Dual (Recording and Control) Capabilities and a Method for Contingent Random, Nonrandom, Turbulent, or Nonturbulent Stimulation for Seizure Blockage."

BACKGROUND OF THE INVENTION

1. Field of the Invention

This invention relates generally to medical apparatus and, more specifically but without limitation, to an electrode apparatus for interacting with the brain of a subject.

2. Description of Related Art

Brain electrical activity (BEA) is a readily accessible and reliable index of brain state and function. It allows distinction between both normal states, such as wakefulness or sleep and its different substates, such as NREM and REM, and abnormal states, such as the ictal and inter-ictal substates of an epileptic brain. BEA is also an important tool for localizing an anatomical substrate of a particular physiological function and for understanding how the function correlates with, or is integrated into, behavior. Brain electrical activity plays a critical role in the evaluation and treatment of pharmaco-resistant, or intractable, epilepsy, movement disorders, and other neurological diseases. Furthermore, BEA is the basis for real-time automated detection and prediction of the clinical onset of seizures as disclosed in U.S. Pat. No. 5,995,868 issued Nov. 30, 1999 to Ivan Osorio et al, which is incorporated herein by reference. Output from such real-time automated detection and prediction of the clinical onset of seizures provides the cue for delivery of suitable therapeutic means for automated blockage of seizures by either contingent or closed-loop therapy. Closed loop therapy would benefit a significant number of persons with pharmaco-resistant epilepsy, thereby improving quality of life and decreasing morbidity, mortality, and cost of care associated with epilepsy. In addition to epilepsy, recordings and analysis of BEA also plays an increasingly important role in the diagnosis and control of a wide variety of other brain disorders.

While recording of electrical activity directly from the cortical surface provides more information than scalp recordings, the current methodology, techniques and devices/probes have important limitations that must be overcome if further advances are to be made in the field of neurosciences in general and of epilepsy in particular. The following brief technical overview provides the anatomical and physiological basis for the understanding of such limitations and for the rationale and justification behind the invention described herein, whose objectives are to enhance signal (BEA) quality and information content, and to control/prevent abnormal or undesired state changes.

The following is intended to provide an understanding of the environment on the present invention:

a) The folding of the cortex of the human brain causes the cortex to be a very complex generator;

b) volume conduction and signal dispersion, which impair the ability to precisely localize the site of origin of electrical activity in the brain, are of high degree at the superficial layers of the cortex (which correspond at most to approximately 0.5 mm of the entire cortical thickness) unlike in deeper parts of the cortex where voltage gradients of up to 10 mV/mm are found in the vertical direction; more specifically, the weight of synaptic relations in the cerebral cortex is in a vertical direction, normal to the cortical surface;

c) deeper cortical layers, especially layer V, are intimately connected with seizure generation and propagation;

d) seizure patterns may be restricted to certain cortical layers and multiple seizure patterns may occur superposed, without influencing one another;

e) signal quality and information content are much lower at the surface than at deeper layers of the cortex. Spikes, the single most important index of potentially epileptogenic tissue, reach maximum voltage in the depths of the cortex where they originate and from where they propagate towards the surface. Similarly, spikes have higher frequencies and richer morphology (higher information content) at the depths of the cortex than at the surface of the cortex. Moreover, information about the time relationship between spikes, which is critically important for detection and control of state change of the brain, is highly accurate at the depths of the cortex and very limited at the surface of the cortex; and f) cortical columns have a diameter of 200–500 nm. Cortical macrocolumns have a diameter ranging between approximately 0.5–3 mm and a height of approximately 2.5 mm. A cortical macrocolumn typically contains approximately $10^5$–$10^6$ neurons. The distance to which cells in the macrocolumn send collaterals is approximately 3 mm, which provides an indication definition of their spatial scale. Minicolumns having a diameter of approximately 20–50 $\mu$m has been proposed as a basic functional unit of neocortex; these dimensions can be defined by the characteristic lateral spread of axons of inhibitory neurons. A minicolum spanning the entire cortical thickness contains approximately one hundred ten neurons lined up along its axis, whereas a striate cortex contains approximately two hundred sixty neurons. Simultaneous interactions can be expected to take place at other spatial scales (for example between neurons, minicolumns, corticocortical columns, cytoarchitectonic regions, etc. An electrode having a tip diameter of $10^{-3}$ cm and placed closed to the body of a neuron records activity contributed by approximately one hundred neurons.

These observations lead to the conclusions that the superficial cortex acts as a filter for the activity of the deeper layers of the cortex and that no prediction as to the site of origin, direction, speed and range of propagation of electrical activity can be made from the cortical surface with a useful degree of accuracy. The intricate cytoarchitecture and gross morphology of the cortex (with folding as its most striking feature) underscore the need and importance to simultaneously record/sense and control activity intracortically and from its surface (epicortex) to improve signal quality, information content, and temporo-spatial resolution. Accomplishing this important objective, requires electrodes/devices not currently available since existing intracranial electrodes, either subdural or depth, have several significant limitations, which limitations as hereinafter described also apply to electrical stimulation of the cortex. Such limitations can be briefly described as follows:

Poor Spatial Resolution

The metal contacts of prior art strip-type electrodes 2, see FIG. 2A, and prior art grid-type electrodes 3, see FIG. 2B, record activity only from areas of the most superficial cortex and which are naturally exposed within the cranial cavity, such as the top or crown of gyri, while approximately two-thirds of the cortex is not accessible to direct surveillance using existing electrodes. Naturally exposed cortices 4 of the gyrus and naturally unexposed cortices 5 of the gyrus are illustrated in FIG. 1. In fact, only about one-third of the cortex and its associated electrical activity are accessible to grid-type or strip-type electrodes. Strip-type and grid-type electrodes that are typically placed on the surface of the cortex. A strip-type electrode 2 can only be used on the exposed cortices 4 of the gyrus.

Depth electrodes 6, see FIG. 2C, another type of sensing devices, are too large for use in the cortex, being better suited for recording from, and stimulation of, subcortical structures such as the amygdala and hippocampus located medially (internally) in the temporal lobe and in other subcortical nuclei such as the thalamus, which differ in several important aspects from the neocortex. Furthermore, even if the diameter of depth electrodes were to be reduced, their ability to localize and track spatio-temporal spread (due to the fact that they would provide only one-dimensional information) would be impaired. Also the possibility of radial migration of these type of electrodes (with consequent loss of the desired target) would remain unaddressed. As a result, prior art recording devices and methods are unable to:

(i) detect, from the surface without contamination or distortion, electrical fields generated below the cortical surface (or intracortically) especially from the deeper layers where generation of electrical signals is most active. Moreover, signals recorded from the surface are highly filtered, which results in shape- and phase-distortions. As a result, signals acquired with prior art devices provide limited and poor quality information about cortical dynamics;

(ii) detect changes which may be close to the recording device but which project only within a very small solid angle;

(iii) precisely localize the critical or primary region from where physiological or pathological activity of interest is generated because it is transmitted with delay, phase distortion, and loss of amplitude and information content to the top of a gyrus. These limitations are due, in part, to the fact that the amplitude of an electrical signal decays as a function of the distance from where it is generated; in other words, the electrical potential at a point behaves according to V~q/r where voltage, V, is proportional to charge, q, and inversely proportional ro r, which is the distance between the generator and the recording electrode. Furthermore, a solid angle, whose magnitude determines the magnitude of an electrical field in a volume conductor as viewed from the surface along the inner walls of the gyri, is virtually zero. More specifically, signals from exposed cortices 4 can be recorded because electrical activity from these surfaces 4 form a measurable solid angle at the recording electrodes as indicated by the angle θ designated by the numeral 7 in FIG. 3, while unexposed cortices 5 do not form a measurable solid angle as indicated by attempting to measure brain electrical activity with a depth electrode 8 from the shaded region designated by the numeral 9 in FIG. 3. Any electrode can record activity only from the surfaces whose solid angle is large enough to be measured by an electrode. The size of the solid angle is a function of the position/orientation and size of the neuronal pool in relation to the electrode used to record its electrical activity. In other words, electrical activity along those walls, which constitute a large portion of the gyrus, is either undetected or inadequately recorded at the surface. The inability to resolve potentially discrete but relevant changes in BEA with high spatial accuracy negatively impacts scientific progress and compromises clinical care in the important areas of epilepsy, neurology, psychiatry, and mapping of cognitive or other functions of the brain; and (iv) extract three-dimensional information since electrical activity is generated and also integrated in three dimensions. Existing devices provide only one-dimensional or two-dimensional information;

Poor Temporal Resolution

Due to the inability of existing devices and methods to record from the depths, walls, and other unexposed surfaces of cortical gyri, there is a variable delay (often reaching infinity) until the electrical activity generated from the unexposed surfaces reaches the crown of the gyri where the recording device is traditionally placed. This translates into the inability to detect, in a timely manner, brain state changes, whether normal or abnormal, unless the changes occur in the immediate vicinity of a contact and the solid angle is large;

Inability to Track Origin and Spatio-Temporal Evolution or Spread of the Signal

Existing strip/grid or depth electrode designs do not allow the simultaneous recording of signals from exposed epicortical (surface) and intracortical regions or from the depths, walls, and other unexposed surfaces of cortical gyri, providing either only one-dimensional or two-dimensional information, thus hampering the ability to localize the origin and track the spatio-temporal evolution of brain state changes, either normal or abnormal, with a useful degree of precision. As opposed thereto, the present invention disclosed herein provides the capability of obtaining reliable three-dimensional information; and Low Signal Amplitude, Spatial Instability, Poor Contact of Strip/Grid Electrodes, and Difficulties with Target Acquisition The stability and degree of contact between the cortex and the recording surfaces of existing recording strip- and grid-electrodes, is limited and inadequate, and usually further decreases as a function of movement and positioning of a subject's head. As a result, the amplitude of the signal is low and of poor quality because when recorded from the cortical surface it depends to some extent on the amount of cerebro-spinal fluid, which acts as a shunt upon the surface of the brain, and the firmness with which the electrode rests upon the cortical surface. Signal degradation occurs because the recording surfaces are not anchored in close contact and in a fixed position relative to the underlying cortex but, instead, "float" over the cerebro-spinal fluid. Also, since the strip- or grid-electrodes in which the recording contacts are embedded enter the cranium at an angle due to the manner in which they are tethered, the contacts closest to the point of entrance are often not in contact with the cortex, while those farthest away from the point of entrance tend to move vertically and laterally, either flapping or fluttering, thereby compromising the quality of both the cortical signal and control capabilities. Furthermore, a strip-electrode inserted through a burr hole often kinks, bends or twists, preventing it from recording from desired regions while potentially increasing the trauma to the cortex, since electrode re-insertions may be required. More specifically, prior art macro-electrodes, such as strip electrode 2, grid-electrode 3 and depth electrode 6 include electrode contacts 10 for recording electrical potentials. However, such prior art electrodes leave much to be desired. For example, a prior art strip electrode is typically inserted into the skull through a burr hole 11, see FIG. 5. The presence of kinks 12 or electrode hanging contacts 13 contribute to contaminated signals, such as that illustrated in FIG. 4B as compared to a good signal as illustrated in FIG. 4A.

Another factor which degrades cortical signals and may considerably limit the ability to control state changes using physical, chemical or other means is the layer of cerebrospinal fluid (CSF) interposed between the cortex and the device or contact; with prior art electrode design, the amount of CSF under the device may be considerable, with certain positions of the head. This layer of CSF shunts electrical currents (in the case of electrical stimulation), or dilutes/washes out chemicals or medicaments delivered to the underlying cortex to control/prevent undesirable or unsafe state changes. Those skilled in the art appreciate that the invention disclosed herein can be used not only for the detection but also for the control/prevention of undesirable state changes since electrical stimulation and induction of temperature changes, among others, can be effected through some of these devices.

What is needed is a mechanism that provides proper continuous close contact between the cortex, both exposed and unexposed, and recording devices thereby considerably increasing the information content of the signal and decreasing noise; that minimizes displacement and flutter or flap of the recording contacts or surfaces thereby limiting recording and/or control signal degradation and loss of target acquisition; that increases the spatial and temporal resolution by providing three-dimensional information to thereby allow for more precise and timely localization of the site of origin and time of onset of brain state changes; that allows more precise, timely and efficacious therapeutic intervention control of brain state changes; that obviates, in certain cases, the need to expose the brain through burr holes or craniotomy thereby minimizing the risk of damage to the cortex, hemorrhage, infection and reducing surgical and anesthesia time; and that improves efficacy by increasing spatial selectivity of stimulation and number of targets resulting in less trauma to brain tissue; that performs functions with a single device that presently requires two or more prior art devices.

SUMMARY OF THE INVENTION

The improvement of the present invention provides an electrode with three-dimensional capabilities for detection and control of brain state changes of a subject that includes a body mechanism having a disk portion having an upper surface and a lower surface, and a shaft portion secured to and extending perpendicularly outwardly from the lower surface of the disk portion, the shaft portion having an outer surface; at least one recording or stimulating contact surface structured to operatively interact with the brain of a subject; and at least one conductor structured to operatively connect each at least one recording or stimulating contact surface in communication with external apparatus. The at least one recording or stimulating contact surface may include one or more recording or stimulating contact surfaces positioned on the lower surface of the disk portion, and one or more recording or stimulating contact surfaces positioned on the outer surface of the shaft portion. One or more of recording or stimulating contact surfaces positioned on the lower surface of the disk portion may be annularly or circularly shaped. Each of the recording or stimulating contact surfaces on the lower surface of the disk portion and the shaft portion is isolated from the other recording or stimulating contact surfaces by insulating material.

A first modified embodiment of the electrode with three-dimensional capabilities for detection and control of brain state changes of a subject of the present invention includes a body mechanism comprising a disk portion having an upper surface and a lower surface, and a hollow shaft portion secured to and extending perpendicularly outwardly from the lower surface of the disk portion, the shaft portion having an inner surface and an outer surface; at least one electrode device pivotally mounted on the inside surface of the hollow shaft portion and having a distal end structured to operatively provide recording or stimulating contact with the brain of a subject; at least one conductor structured to operatively and separately connect the distal end of each at least one electrode device in communication with external apparatus; and at least one activating mechanism structured to operatively and selectively cause a respective at least one electrode device to insert and retract the corresponding distal end into and from brain tissue of the subject spaced adjacent thereto. The first modified embodiment of the present invention may also include at least one recording or stimulating contact surface positioned on the outer surface of the hollow shaft portion; and at least one conductor structured to operatively and separately connect each at least one recording or stimulating contact surface in communication with external apparatus. In addition, the at least one activating mechanism of the first modified embodiment of the present invention may include a pair of control wires trained through the center opening wherein one of the pair of control wires causes the distal end of the respective at least one electrode device to be inserted into brain tissue of the subject spaced adjacent thereto and the other one of the pair of control wires causes the distal end of the respective at least one electrode device to be retracted from brain tissue of the subject spaced adjacent thereto. Alternatively, the at least one activating mechanism may include a stepper motor structured to operatively and selectively cause the distal end of a respective at least one electrode device to be inserted into and retracted from brain tissue of the subject spaced adjacent thereto.

A second modified embodiment of the electrode with three-dimensional capabilities for detection and control of brain state changes of a subject of the present invention includes a body mechanism comprising a disk portion having an upper surface and a lower surface, and a solid shaft portion secured to and extending perpendicularly outwardly from the lower surface of the disk portion, the shaft portion having an outer surface; at least one channel formed in the disk portion and solid shaft portion wherein each at least one channel has an upper end and a lower end and wherein the upper end exits generally perpendicularly from the upper surface of the disk portion and the lower end exits generally perpendicularly from the outer surface of the solid shaft portion; at least one electrode wire structured to be operatively and slidably inserted through the at least one channel such that a distal end of the electrode wire can be selectively inserted into brain tissue of the subject spaced adjacent to the lower end of the respective channel. The second modified embodiment of the present invention may also include a cannula slidably inserted through each at least one channel between the at least one channel and the electrode wire therein, such that the cannula and the electrode wire are separately and selectively lengthwise slidable relative to each other and to the channel. Further, the second modified embodiment of the present invention may include a first activating mechanism for separately extending and retracting the at least one cannula relative to both the respective channel and electrode wire therethrough to extend and retract the respective distal end of the cannula into and from brain tissue spaced adjacent to the lower end of the respective channel; and a second activating mechanism for separately extending and retracting the electrode wire relative to the respective channel and cannula to extend and retract the respective distal end of the electrode wire into and from brain tissue spaced adjacent to the lower end of the respective channel.

A third modified embodiment of the electrode with three-dimensional capabilities for detection and control of brain state changes of a subject of the present invention includes a body mechanism comprising a plate portion having an upper surface and a lower surface, and a plurality of shaft portions secured to and extending perpendicularly outwardly from the lower surface of the plate portion; each shaft portion having an outer surface; at least one recording or stimulating contact surface positioned on the outer surface of at least one of the plurality of shaft portions, the at least one recording or stimulating contact surface structured to operatively interact with the brain of a subject; and at least one conductor structured to operatively connect a different one of each at least one recording or stimulating contact surface in communication with external apparatus. In addition, the third modified embodiment of the present invention may include one or more recording or stimulating contact surfaces positioned on the lower surface of the plate portion.

PRINCIPAL OBJECTS AND ADVANTAGES OF THE INVENTION

The principal objects and advantages of the present invention include: providing a mechanism that ensures proper continuous close contact of constant degree between the cortex, both exposed and unexposed, and recording devices thereby considerably increasing the information content of the signal and decreasing noise for improved recording and control purposes; providing such a mechanism that minimizes displacement and flutter or flap of the recording contacts or surfaces thereby limiting recording and/or control signal degradation and loss of target acquisition; providing such a mechanism that considerably increases the spatial and temporal resolution by providing three-dimensional information to thereby allow for more precise and timely localization of the site of origin and time of onset of brain state changes; providing such a mechanism that allows more precise, timely and efficacious therapeutic intervention control of brainx state changes; providing such a mechanism that obviates, in certain cases, the need to expose the brain through burr holes or craniotomy thereby minimizing the risk of damage to the cortex, hemorrhage, infection and reducing surgical and anesthesia time; providing such a mechanism that improves efficacy by increasing spatial selectivity of stimulation and number of targets resulting in less trauma to brain tissue than that caused by prior art methods; providing such a mechanism that perform functions with a single device that presently requires two or more prior art devices, such as a strip- or grid-electrode in combination with a depth electrode which may not safely and satisfactorily perform; and generally providing such a mechanism that is reliable in performance, capable of long lasting life, and particularly well adapted for the proposed usages thereof.

Other objects and advantages of this invention will become apparent from the following description taken in conjunction with the accompanying drawings wherein are set forth, by way of illustration and example, certain embodiments of this invention.

BRIEF DESCRIPTION OF THE DRAWINGS

FIG. 6A depicts an enlarged, top and side perspective view of a unitized electrode with three-dimensional capabilities for detection and control of brain state changes, the electrode having a recording and/or stimulating contact surface in accordance with the present invention.

FIG. 6B depicts an enlarged, bottom and side perspective view of the unitized electrode with three-dimensional capabilities for detection and control of brain state changes of FIG. 6A.

FIG. 6C depicts enlarged views of the unitized electrode with three-dimensional capabilities for detection and control of brain state changes, showing one of the electrodes of FIG. 6A inserted directly into the subject's brain and another one of the electrodes of FIG. 6A inserted into a fold of the gyrus.

FIG. 6D depicts an enlarged, top and side perspective view of a variation of the unitized electrode with three-dimensional capabilities for detection and control of brain state changes, the electrode having a shaft with multiple recording and/or stimulating contact surface electrodes separated by insulating material and separately accessible by independent conductors.

FIG. 6E depicts an enlarged, bottom and side perspective view of another variation of the unitized electrode with three-dimensional capabilities for detection and control of brain state changes, the electrode having a shaft similar to the shaft of the variation of FIG. 6D, but also including multiple annular-shaped recording and/or stimulating contact surfaces located on a bottom surface of a disc portion thereof wherein each contact surface is separated by insulating material and is separately accessible by independent conductor.

FIG. 6F depicts an enlarged, bottom and side perspective view of yet another variation of the unitized electrode with three-dimensional capabilities for detection and control of brain state changes, the electrode having a shaft similar to the shaft of the variation of FIG. 6D, but also including multiple circularly-shaped recording and/or stimulating contact surfaces located on the bottom of the disc portion wherein each contact surface is separated by insulating material and is separately accessible with an independent conductor.

FIG. 7 depicts an enlarged cross-sectional view of a first modified embodiment of the unitized electrode with three-dimensional capabilities for detection and control of brain state changes according to the present invention, wherein a plurality of pivotally mounted electrodes of the present invention are combined in a single macroelectrode inserted into a fold of the gyrus.

DETAILED DESCRIPTION OF THE PREFERRED EMBODIMENTS

Figure 1:
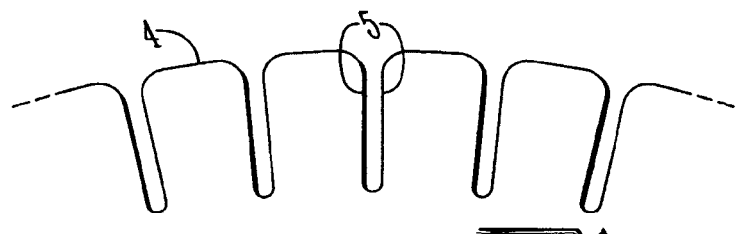
FIG. 1 depicts an enlarged view of the cortex of a human brain showing exposed and unexposed portions thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 20 generally refers to a unitized electrode with three-dimensional capabilities for detection and control of brain state changes in accordance with the present invention, as shown in FIGS. 6A through 6F. FIGS. 6A and 6B show an enlarged top and side perspective view and an enlarged bottom and side perspective view, respectively, of an electrode 20 having a "tack"-like configuration with a disk portion 22, a shaft portion 24, and conductors 26, such as electrically conducting wires or other suitable arrangement as appropriate for a particular application as hereinafter disclosed. The shaft portion 24 is secured to, or formed integrally with, the disk portion 22 and generally extends perpendicularly outwardly from the disk portion 22, preferably from the center thereof. For some applications, however, it may be desirable that the shaft portion 24 be spaced off-center and/or at a selected angle relative to the disk portion 22. The shaft portion 24 is generally inserted in a radial direction, i.e., parallel to the orientation of apical dendrites or of the fibers (axons) entering or leaving the cortex at that site. In some applications, however, the shaft portion 24 may be inserted orthogonally or obliquely into the cortex. The direction of insertion is a function of the site selected for recording or control of brain state changes. This approach is favored over others, such as anchoring the device to the dura mater or to the skull, because it increases the area of recording surfaces and minimizes tearing of the cortex and dura that may result from differential displacement of these structures associated with head movements of certain force/acceleration and direction. The disk portion 22 has an upper surface 28 and a lower surface 30. The shaft portion 24 has an outer surface 32. As shown in FIGS. 6A and 6B, the outer surface 32 of the shaft portion 24 has a single recording and/or stimulating contact surface 32 thereon connected in communication with conductor 26. Alternately, the shaft portion 24 may have a plurality of bands of recording and/or stimulating contact surfaces 36 separated by insulating material 38, as indicated in FIGS. 6D and 6F. In that event, each of the recording and/or stimulating surfaces 36 is independently connected to a different one of the conductors 26. In addition, the lower surface 30 of the disk portion 22 may have a single recording and/or stimulating contact surface 40 connected in communication with a separate one of the conductors 26. Alternately, the disk portion 22 may have one or more concentric annularly-shaped bands of recording and/or stimulating contact surfaces 42 separated by insulating material 44, as indicated in FIG. 6E. In that event, each of the recording and/or stimulating contact surfaces 42 is independently connected to a different one of the conductors 26 and independently of conductors 26 connected to the bands of recording and/or stimulating contact surfaces 36 on the outer surface 32 of shaft portion 24. For some applications, it may be desirable to use one or more circularly-shaped recording and/or stimulating contact surfaces 46 separated by insulating material 48 in place of some or all of the previously described annularly-shaped bands of recording and/or stimulating contact surfaces 42, as depicted in FIG. 6F.

Generally, the disk portion 22 has a diameter between approximately 1–25 mm and the shaft portion 24 has a diameter between approximately 0.1–1.0 mm; it is to be understood, however, that the disk portion 22 and the shaft portion 24 may have other dimensions as necessary for a particular application. The length of the shaft portion 24 may have any desired length depending on the location as required for a particular application, as shown in FIG. 6C, wherein one of the electrodes 20 is inserted directly into brain tissue, designated by the numeral 50, and another one of the electrodes 20 in inserted into a fold of the gyrus, designated by the numeral 52. FIG. 6C illustrates how the electrode 20 can be inserted into the fold of the gyrus so that it can record from the unexposed surfaces, which project a negligible solid angle onto electrodes placed on the surface of the cortex. Another advantage of electrode 20 is that the arrangement of the disk portion 22 and the shaft portion 24 relative to each other provide each other with the anchoring needed to maintain good contact and stable target acquisition, thereby improving signal-to-noise ratio, detection performance and efficacy of control measures.

In other words, electrode 20 may be inserted into the exposed cortex or into the folds to record from both unexposed cortex and from the depths of the cortex. The insertion of the shaft portion 24 either directly into brain tissue or into a fold of the gyrus stabilizes the electrode 20 and prevents undesired lateral movement of the contact surfaces 40 on the lower surface 30 of the disk portion 22 relative to the exposed surface of the cortex which the contact surfaces 40 are bearing against. Concurrently therewith, the abutting engagement between the lower surface 30 of the disk portion 22 stabilizes the electrode 20 and prevents undesired axial movement of the contact surfaces 36 of the shaft portion 24 relative to brain tissue. In other words and as one skilled in the art can determine from this disclosure, the presence of disk portion 22 provides supporting and anchoring capabilities to the shaft portion 24 and prevents undue movement of the shaft portion 24 to thereby avoid the consequent noise and contaminated signals as experienced with the use of prior art devices. Similarly, the presence of the shaft portion 24 provides an anchor to the contact surfaces of the disk portion 22 to prevent movement artifacts.

Figure 2A:
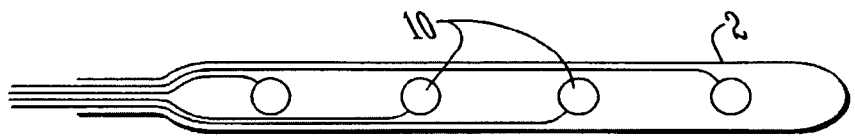
FIGS. 2A–2C depict enlarged views of prior art strip-, grid- and depth-electrodes, respectively.
Figure 2B:
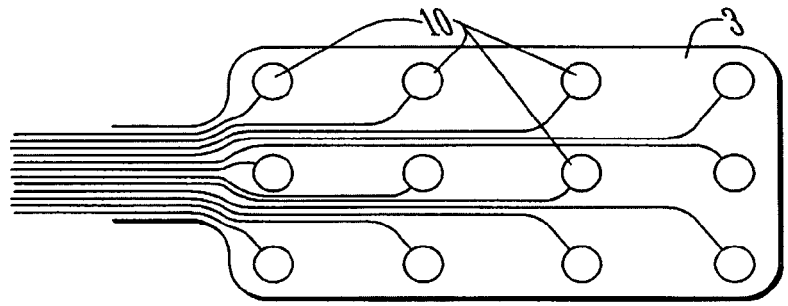
Figure 2C:
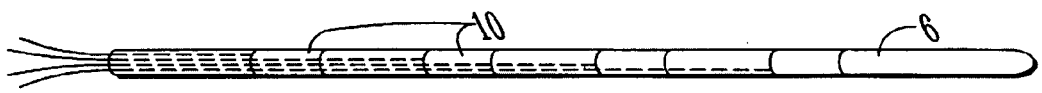
Figure 3:
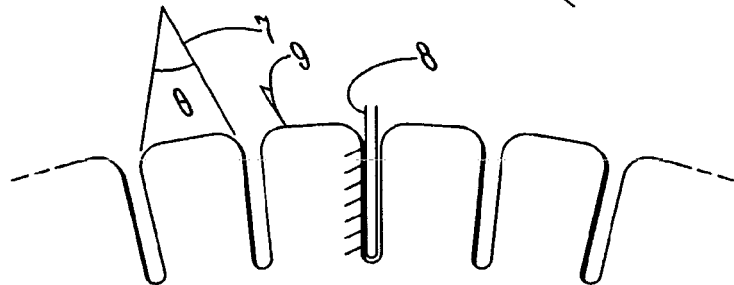
FIG. 3 depicts an enlarged view, similar to FIG. 1, illustrating characteristic electrical activity near surface and depth electrodes.
Figure 4A:
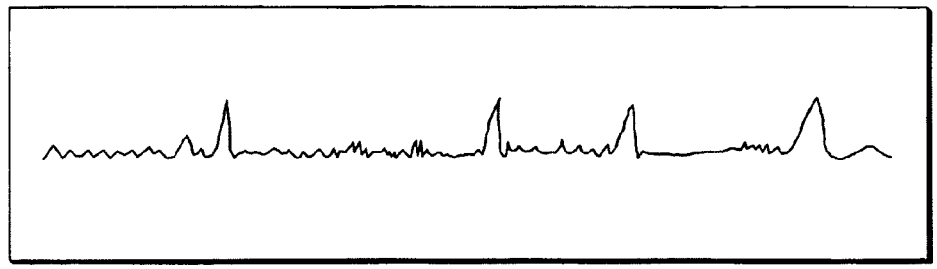
FIGS. 4A–4B depicts examples of a good (uncontaminated) signal and a noisy (contaminated) signal, respectively, wherein the noisy signal arises from movement of a prior art electrode due to inadequate anchoring.
Figure 4B:
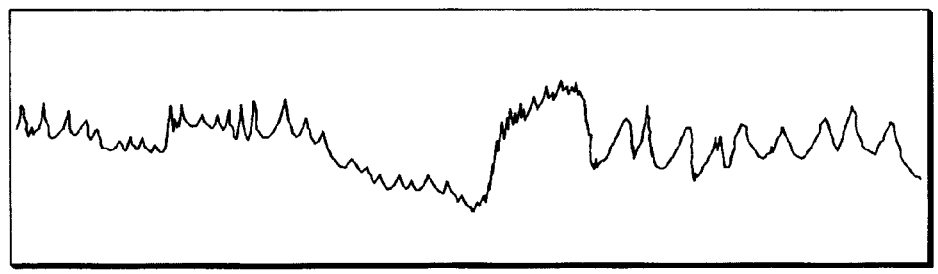
Figure 5:
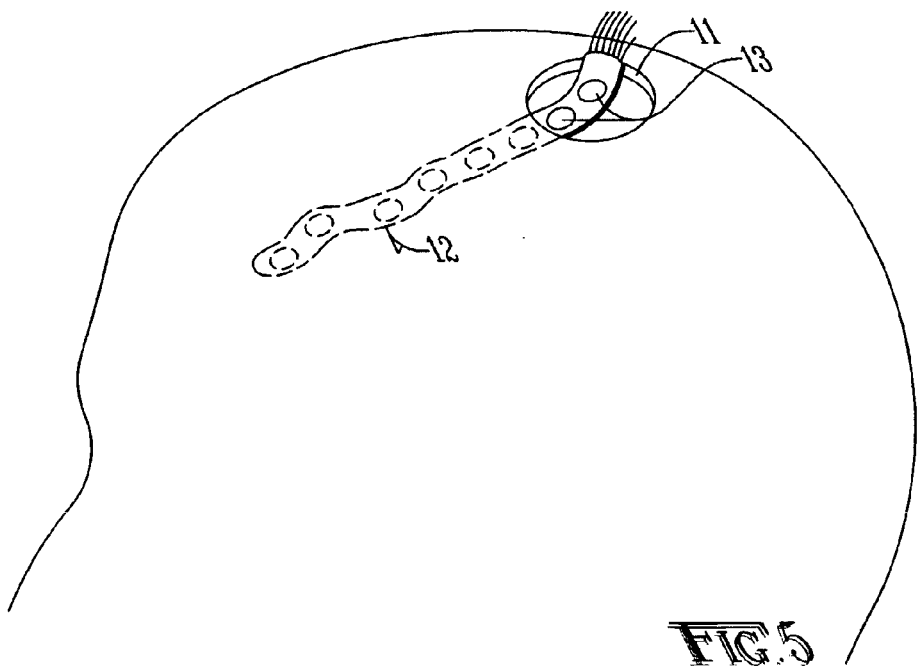
FIG. 5 depicts a prior art strip-electrode typically placed on the cortical surface through a burr hole indicating areas where the electrode may not have proper communication with the brain of a subject due to improper contact or kinks, either one of which may result in poor signal quality as depicted in FIG. 4B.

Electrode 20 is sometimes referred to herein as a mesoelectrode because the diameter of the shaft is between the dimensions of the microelectrodes for single unit or intracellular recordings and the depth macro electrodes shown in FIG. 2. Depending on the diameter of the shaft portion 24, the present invention records activity ranging from minicolumns which correspond approximately to $10^2$ neurons which constitute a minicolumn (for diameters of ~0.1 mm) to possibly up to $10^5$–$10^6$ neurons which constitute a macrocolumn; that is, the mesoelectrode of the present invention can simultaneously record activity from multiple spatial scales. Those skilled in the art realize that the mesoelectrode electrode can have two or more shaft portions as required for a particular application. The mesoelectrode can be inserted, as shown in 6A, into the exposed cortex or into the folds of the cortex to record from unexposed cortex and from its depths. This macroelectrode can be used for subcortical structures but not for cortical recordings. An electrode having a tip diameter of $10^{-3}$ cm and placed closed to the body of a neuron records activity contributed by approximately one hundred neurons.

Electrode 20 is constructed of biocompatible materials, such as polyurethane covered as appropriate with thin sheets or coatings of noble metals, such as platinum or other suitable material. The shaft portion 24 of the mesoelectrode 20 is configured to operatively accept a rigid mandrel to guide the electrode 20 into the brain tissue. The various contact surfaces are constructed of inert but conductive materials, such as platinum or platinum-iridium or other suitable material. If desired, contact surfaces of the disk portion 22 and shaft portion 24 may be "printed" or deposited onto the respective underlying surfaces using photolithographic techniques. In the case of the circularly-shaped contacts 46 shown in FIG. 6F, the diameter thereof generally ranges between approximately 1–5 mm and the contacts of the shaft portion 24 may be of any suitable length. Insulating material between the various contact surfaces is constructed of biologically inert material, such as polyurethane or other suitable material, to prevent adjacent contacts from touching each other, which could otherwise create an undesirable "shunt". Conductors 26, passing through the shaft and protruding from the upper surface 28 of the disk portion 22, transfer signals from the various contact surfaces to amplifiers, usually for recording purposes, and are constructed of electrically conductive material, such as copper or other suitable material. Electrical insulation is present about the conductors 26 throughout the shaft portion 24 and continues up to the juncture between the conductors 26 and the corresponding contact surface. Conductors or wires 26 may also be used to convey control signals from control units (or stimulation units) to selected ones of the contact surfaces. Each individual contact surface of the disk portion 22 and shaft portion 24 is connected to an electrically distinct conductor 26 allowing any contact surface to be independently available for stimulation either synchronously or asynchronously. For some applications, it may be desirable that communication to and from the electrode 20 be wireless, through micro- or nano-telemetric devices, housed in, or spaced in close proximity to, the electrode 20. The presence of the contact surfaces of the disk portion 22 and the shaft portion 24 in three distinct axes provides three-dimensional information gathering capability for brain electrical activity (BEA) and thus improves over the capabilities of the prior art devices for analysis of brain signals. The presence of multiple contacts on the shaft portion 24 and on the disk portion 22 improves the temporal and spatial resolution of cortical signals and also of the therapy delivered to the cortex, which translate into improved detection and control of brain state changes. The various contact surfaces that are connected to control units through conductors 26 not only allow usage of electrical stimulation strategy but also allow other therapeutic modalities such as cooling. Those skilled in the pertinent art will appreciate that the mesoelectrode may be constructed using ceramic or silicon and thin-film techniques.

A first modified embodiment of the unitized electrode with three-dimensional capabilities for detection and control of brain state changes, designated by the numeral 60, is depicted in FIG. 7. The first modified embodiment 60 includes a hollow body mechanism 61 having one or more retractable electrode devices 62 with distal ends 63 that can be selectively pushed out into the cortex, wherein the body mechanism 61 is secured to a disk portion 64 similar to that hereinbefore described for electrode 20. Disk portion 64 provides supporting and stabilizing structure for the first modified embodiment 60 but can also have one or more recording and stimulating contact surfaces on a lower surface 65 thereof, as hereinbefore described. While the body mechanism 61 is being inserted into a fold of the gyrus, as indicated in FIG. 7, the distal ends 63 of the retractable electrode devices 62 are retained within the body mechanism 61. Once the body mechanism 61 is suitably placed inter-gyrally as desired, i.e., in between two lateral walls of the brain, levers 66 can be operated by pairs of control leads or wires 67 to cause the distal ends 63 of the electrode devices 62 to the pushed into the brain tissue adjacent thereto. The levers 66 are mounted on an inner surface 68 of the body mechanism 61. The control wires 67 can be operated manually, in which case pulling one of the pair of wires 67 extends the associated distal end 63 into the tissue and pulling the other one of the pair of wires 67 retracts the associated distal end 63 into the body mechanism 61. It is to be understood that other precision control means, such as using stepper motors, dc motors or other suitable mechanisms may also be used for the purpose of extending and retracting the distal ends 63 into and from the adjacent brain tissue. If stepper motors are used, the control wires are attached to the stepper motor shaft so that rotating the motor in one direction (for example, clockwise) pushes the distal end into the brain tissue while rotating the motor in the opposite direction (for example, counterclockwise) retracts the distal end back into the shaft. It is to be understood that the stepper motors may be positioned outside the electrode structure. While any stepper motor can be used, use of one or more micro-stepper motors allows precise positioning of the distal ends 63. For example, micro-stepper motors can be used to advance the distal ends 63 into the tissue in small steps for precise positioning thereof. Either separate motors can be used to control each distal end 63 separately, or one motor can be used to simultaneously extend/retract some or all of the distal ends 63 as desired for a particular application. Although only three electrode devices 62 are shown in FIG. 7, any number of the electrode devices 62 can be used to obtain as much spatial resolution as desired. The presence of several of the electrode devices 62 spaced around the body mechanism 61 provides three-dimensional information of the BEA. The distal ends 63 of the electrode devices 62 are connected in communication with conductors 69 that can be used for recording the BEA. It is to be understood that one or more contact surfaces 71 on an outer surface of the body mechanism 61, as hereinbefore described, may be used in combination with the electrode devices 62 for a particular application as needed.

Figure 8A:
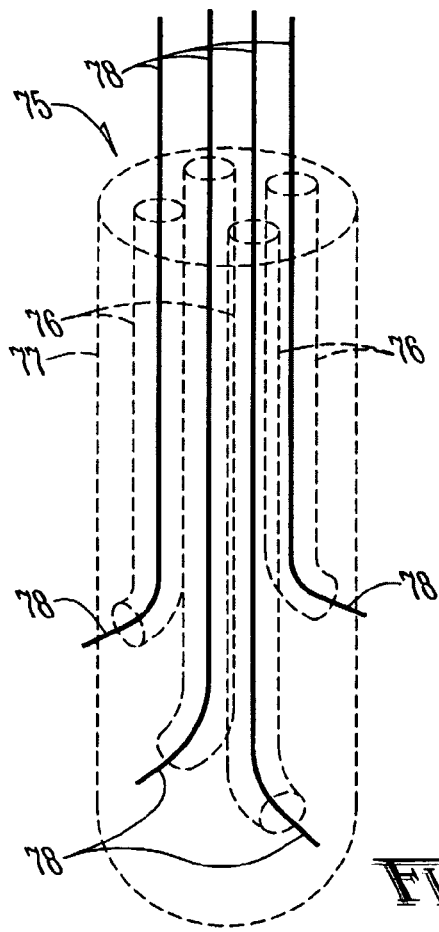
FIG. 8A depicts an enlarged view of a second modified embodiment of the unitized electrode with three-dimensional capabilities for detection and control of brain state changes according to the present invention, wherein a plurality of channels are formed in a solid shaft for slidably receiving electrode wires therethrough.
Figure 8B:
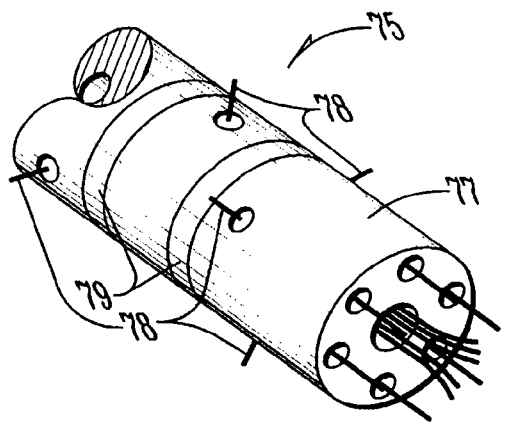
FIG. 8B depicts an enlarged perspective end view of a variation of the second modified embodiment, similar to that shown in FIG. 8A, but having a plurality of independent surface electrodes positioned on an outer surface of the solid shaft.

A second modified embodiment 60 of the unitized electrode with three-dimensional capabilities for detection and control of brain state changes, designated by the numeral 75, is shown in FIGS. 8A and 8B, wherein channels 76 formed in a body mechanism 77 are utilized to slidably insert electrode wires 78 therethrough. The body mechanism 77 is constructed to insulate the electrode wires 78 from each other, such as by constructing the body mechanism 77 from insulating material, such as polyurethane or the like or lining the channels 76 with insulating material. An application of embodiment 75 can be described as follows: First the body mechanism 77 is inserted as desired into a fold of the gyrus. Distal ends of the electrode wires 78 are slidably pushed through the channels 76 into the brain tissue as desired once the body mechanism 77 is in place. As hereinbefore described, it is to be understood that one or more contact surfaces 79 on an outer surface of the body mechanism 77 may be used in combination with the electrode wires 78 for a particular application as needed.

Figure 8C:
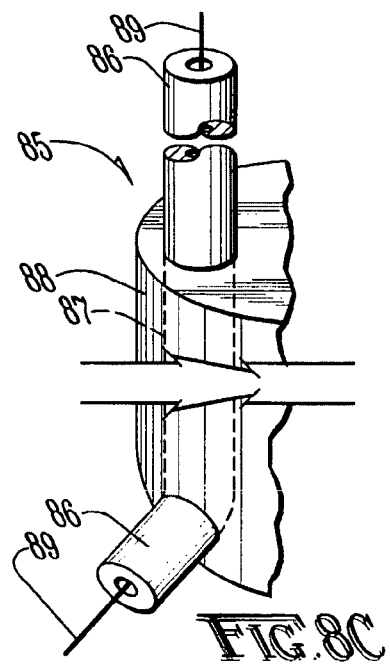
FIG. 8C depicts a fragmentary and schematic illustration of a variation of the second modified embodiment of the present invention as shown in FIG. 8A wherein one or more of the electrode wires is slidably sheathed in a respective cannula slidably inserted through a respective one of the channels.
Figure 8D:
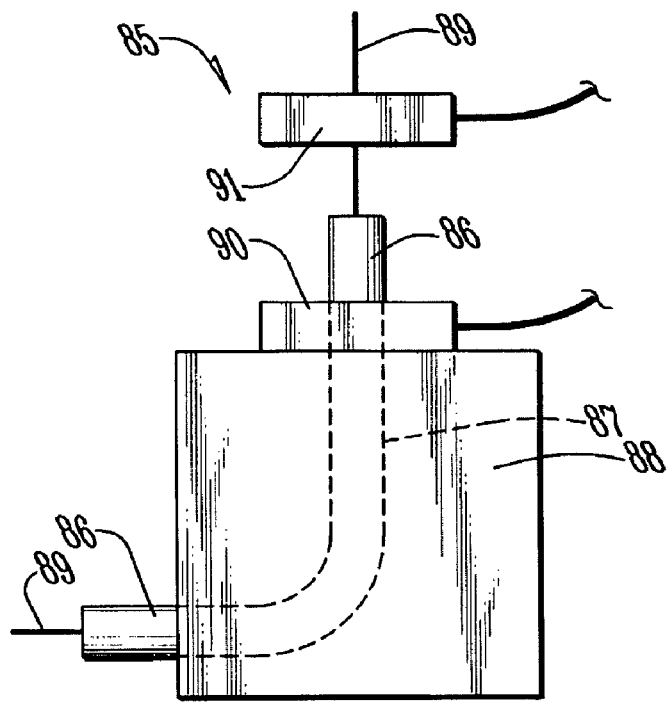
FIG. 8D is a schematic illustration of a motor arrangement for extending/retracting one of the conductor wires and/or cannula of the second modified embodiment of FIG. 8C.

A fragmentary and schematic illustration of a variation of the second modified embodiment 60 of the unitized electrode with three-dimensional capabilities for detection and control of brain state changes, designated by the numeral 85, is shown in FIG. 8C, wherein a cannula 86 is slidably inserted through each channels 87 formed in body mechanism 88 and an electrode wire 89 is slidably inserted therethrough. An application of embodiment 85 can be described as follows: First the body mechanism 88 is inserted as desired into a fold of the gyrus. The cannula 86 is then pushed into the brain tissue as desired once the body mechanism 88 is in place. The cannula 86 is more rigid than the electrode wire 89, thus enabling easier access and penetration into the brain tissue. After inserting the distal end of the cannula 86 a desired distance into the adjacent brain tissue, the more flexible (less rigid) electrode wire 89 is then guided and directed by the inserted cannula 86 as the electrode wire 89 is slidably extended through the cannula 86, at least to the outer extremity of the distal end of the cannula 86. Without displacing the inserted electrode wire 89, the cannula 86 is then retracted into the body mechanism 88, thereby exposing the brain tissue to only the distal end of the electrode wire 89. Due to the elasticity of the brain tissue, the brain tissue closes around the distal end of the electrode wire 89 to form and maintain good communication contact therebetween after the cannula 86 is retracted. It is to be understood that the body mechanism 88 may contain several channels 87, each having a cannula 86 and electrode wire 89 therein as described. Also as hereinbefore described and illustrated, it is to be understood that one or more contact surfaces on an outer surface of the body mechanism 88 may be used in combination with the electrode wires 89 for a particular application as needed.

FIG. 8C is an enlarged and schematic illustration of a first activating mechanism 90, such as a stepper motor, being used to slidably displace the cannula 86 through the channel 87 and a second activating mechanism 91 being used, independently of the first activating mechanism 90, to slidably displace the electrode wire 89 through the cannula 86.

A variation of the present invention is referred to herein as a "hybrid" as it consists of a macroelectrode having a diameter of approximately 1.1–2 mm with its own external recording surfaces, containing internally disposed mesoelectrodes having diameters of approximately 0.1–1 mm which can be deployed to increase dimensionality of recording from one-dimensional to up to three-dimensional. These hybrid electrodes are designed for detection and control of states of subcortical structures (i.e, hippocampus) offering great flexibility, wherein the mesoelectrodes will be deployed only if improved localization signal quality or control are needed.

Figure 9:
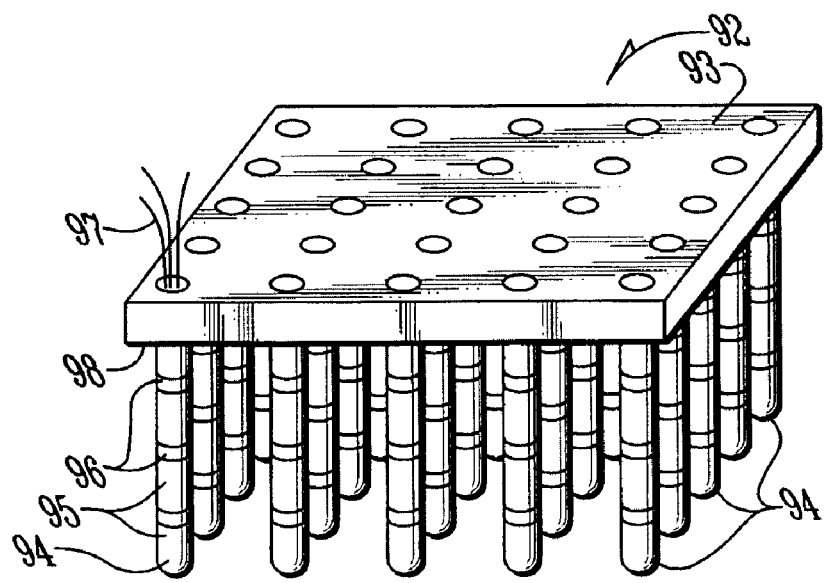
FIG. 9 depicts an enlarged view of a third modified embodiment of the unitized electrode with three-dimensional capabilities for detection and control of brain state changes, the third modified embodiment having a plurality of independent recording and/or stimulating contact surfaces interposed between an array of shafts, each having multiple recording and/or stimulating contact surfaces separated by insulating material and separately accessible with independent conductors for obtaining and recording three-dimensional information from the subject's brain in accordance with the present invention.

A third modified embodiment of the unitized electrode with three-dimensional capabilities for detection and control of brain state changes, designated by the numeral 92 is shown, in FIG. 9. The third modified embodiment 92 includes a plate portion 93 and a plurality of shaft portions 94. As hereinbefore described, each shaft portion 94 may have a plurality of recording and/or stimulating electrode surfaces 95 separated by insulating material 96, as indicated on only one of the shaft portions 94 for simplification of illustration. Each of the recording and/or stimulating electrode surfaces 95 is independently connected to a different one of the conductors 97. In addition, the lower surface 98 of the plate portion 93 may have a single recording and/or stimulating contact surface connected in communication with a separate one of the conductors 97. Application of the third modified embodiment is substantially similar to that indicated in FIG. 6C for electrode 50. The multiple shaft portions 94 allow a further improved three-dimensional resolution of the BEA. For some applications, it may be desirable that a plurality of the cannulae be slidably nested one within another to extend farther into the brain tissue.

Summarizing, those skilled in the art realize that: a) the shape of the electrode component resting over the cortical surface 4 (which in the preferred embodiment for a disk-type embodiment of the present invention) may have any desired shape as appropriate for any particular application, such as rectangular, square, etc. Moreover, the shape thereof may be tailored to conform to the top or exposed part of a gyrus over which it will be placed; b) the electrode may be constructed of materials with high thermal and electrical conductivity such as carbon nanotubes; and c) the shape, size and number of contact surfaces and number, diameter and lengths of the shafts may vary with the application for which it is being used.

Considerable improvements in temporo-spatial resolution, stability of target coverage and of signal acquisition, higher signal/noise ratio of brain signals, and multi-site recording and control capabilities at two or more spatial scales are provided by the present invention comprising a unitized electrode. Through simple changes in design and variations in its length, the device of the present invention can be used for recording of: (i) intra-cortical activity only; (ii) activity from exposed or non-exposed cortical surfaces only; (iii) simultaneous recording of intracortical and epicortical (surfaces) activities from the same or different regions; (iv) inter-gyral activity from non-exposed cortical walls only; (v) inter-gyral and intracortical activities simultaneously; (vi) trans-hemispheric activity from cortical surfaces, intra-cortical regions, white matter and sub-cortical hemispheric structures/nuclei, such as the thalamus, increasing its anatomo-functional range for detection and control of state changes. The multi-site and multi-modal (electrical, thermal, chemical optical or other classes of signals) recording and control capabilities/functions can be applied congruously wherein recording and control are performed through the same device or portion thereof, or incongruously wherein recording and control are carried out either through different portions of the same device or through different devices. Furthermore, such unitized functions can be performed either synchronously in time, or asynchronously in time. Also, detection of brain state changes may be accomplished using electrical or chemical signals and control may be exerted by, for example, cooling the region of interest.

Since the reciprocal projections between the cortex and deep nuclei, such as the thalamus, follow a radial pattern, the device of the present invention allows recording and control of signal/brain states along different levels of the same region/domain in a simultaneous or sequential fashion. Application of additional devices allows similar degrees of flexibility and multiplicity of functions over different regions.

The invention disclosed herein is more efficient and causes less trauma than prior art by requiring fewer electrodes and tissue penetrations and smaller holes, than the previously-required burr holes, for implantation. It is also more cost-effective in that it requires shorter surgical time compared to prior art approaches.

The present invention may also be used for detection purposes as taught in U.S. Pat. No. 5,995,868 issued Nov. 30, 1999 to Ivan Osorio et al.

To summarize, by using the invention disclosed herein, recording/sensing or control of state changes can be performed integrally (across all regions/domains sampled by one or more devices) or differentially (selected regions/domains sampled by one or more devices).

It is to be understood that while certain forms of the present invention have been illustrated and described herein, it is not to be limited to the specific forms or arrangement of parts described and shown.

The invention claimed is:

1. An electrode with three-dimensional capabilities for detection and control of brain state changes of a subject, comprising:
   (a) a body mechanism including:
      (1) a disk portion having an upper surface and a lower surface, and
      (2) a shaft portion secured to and extending perpendicularly outwardly from the lower surface of the disk portion; the shaft portion having an outer surface;
   (b) at least one recording or stimulating contact surface structured to operatively interact with the brain of a subject; and
   (c) at least one conductor structured to operatively connect each at least one recording or stimulating contact surface in communication with external apparatus; and
   (d) wherein the at least one recording or stimulating contact surface is positioned on the lower surface of the disk portion.

2. The electrode as described in claim 1 wherein the at least one recording or stimulating contact surface includes an annularly shaped recording or stimulating contact surface.

3. The electrode as described in claim 1 wherein the at least one recording or stimulating contact surface includes a circularly shaped recording or stimulating contact surface.

4. The electrode as described in claim 3 wherein the at least one recording or stimulating contact surface has a diameter between approximately 1–5 mm.

5. An electrode with three-dimensional capabilities for detection and control of brain state changes of a subject, comprising:
   (a) a body mechanism including:
      (1) a disk portion having an upper surface and a lower surface, and
      (2) a shaft portion secured to and extending perpendicularly outwardly from the lower surface of the disk portion; the shaft portion having an outer surface;
   (b) at least one recording or stimulating contact surface structured to operatively interact with the brain of a subject; and
   (c) at least one conductor structured to operatively connect each at least one recording or stimulating contact surface in communication with external apparatus; and
   (d) wherein the at least one recording or stimulating contact surface comprises a plurality of recording or stimulating contact surfaces separated by insulating material; and
   (e) wherein at least one of the plurality of recording or stimulating contact surfaces is positioned on the lower surface of the disk portion.

6. An electrode with three-dimensional capabilities for detection and control of brain state changes of a subject, comprising:
   (a) a body mechanism including:
      (1) a disk portion having an upper surface and a lower surface, and
      (2) a shaft portion secured to and extending perpendicularly outwardly from the lower surface of the disk portion; the shaft portion having an outer surface;
   (b) at least one recording or stimulating contact surface structured to operatively interact with the brain of a subject; and
   (c) at least one conductor structured to operatively connect each at least one recording or stimulating contact surface in communication with external apparatus; and
   (d) wherein the disk portion and the shaft portion are structured to simultaneously record both from an exposed surface of the cortex and from depths of the cortex of the brain of a subject.

7. An electrode with three-dimensional capabilities for detection and control of brain state changes of a subject, comprising:
   (a) a disk portion having an upper surface and a lower surface, and
   (b) a shaft portion secured to and extending perpendicularly outwardly from the lower surface of the disk portion; the shaft portion having an outer surface;
   (c) a plurality of recording or stimulating contact surfaces structured to operatively interact with the brain of a subject; at least one of the plurality of recording or stimulating contact surfaces positioned on the lower surface of the disk portion and having a circular or annular shape; at least one of the plurality of recording or stimulating contact surfaces positioned on the outer surface of the shaft portion;

(d) insulating material isolating each of the plurality of recording or stimulating contact surfaces from each other; and
(e) at least one conductor structured to operatively and separately connect each of the plurality of recording or stimulating contact surfaces in communication with external apparatus; and wherein the disk portion and the shaft portion are structured relative to each other to operatively provide support and anchoring for each other while providing three-dimensional capabilities for detection and control of brain state changes of a subject.

* * * * *